United States Patent [19]
Ueda

[11] Patent Number: 5,302,104
[45] Date of Patent: Apr. 12, 1994

[54] RESIN DENTURE BASE MOLDING APPARATUS

[75] Inventor: Noboru Ueda, Toyonaka, Japan

[73] Assignee: High Dental Service Co., Ltd., Osaka, Japan

[21] Appl. No.: 900,391

[22] Filed: Jun. 18, 1992

[51] Int. Cl.$^5$ ............................................. A61C 13/20
[52] U.S. Cl. ...................... 425/178; 249/54; 264/17; 425/542; 425/DIG. 11
[58] Field of Search ............... 249/54; 264/17, 18; 425/129.1, 175, 176, 178, 542, 543, 544, DIG. 11

[56] References Cited

U.S. PATENT DOCUMENTS

| | | | |
|---|---|---|---|
| 1,974,663 | 9/1934 | May | 425/178 |
| 2,551,932 | 5/1951 | Dimmer | 264/17 |
| 2,576,224 | 11/1951 | Hordes | 264/17 |
| 2,592,376 | 4/1952 | Ballard | 249/54 |
| 2,660,758 | 12/1953 | Hennike et al. | 425/178 |
| 2,948,018 | 8/1960 | Hintermann et al. | 264/17 |

FOREIGN PATENT DOCUMENTS

| | | |
|---|---|---|
| 841329 | 7/1949 | Fed. Rep. of Germany. |
| 8608409 | 5/1986 | Fed. Rep. of Germany. |
| 2495052 | 6/1982 | France. |
| 2525104 | 10/1983 | France. |
| 56-084930 | 7/1981 | Japan. |
| 58-067428 | 4/1983 | Japan. |
| 721326 | 1/1955 | United Kingdom ................. 264/18 |

Primary Examiner—Jay H. Woo
Assistant Examiner—James P. Mackey
Attorney, Agent, or Firm—Armstrong, Westerman, Hattori, McLeland & Naughton

[57] ABSTRACT

An improved resin denture base molding apparatus for molding denture bases by injecting fused resin R into a denture base plaster mold formed in a flask F, wherein the improvement includes a table 2 provided in a manner capable of elevating up and down along a plurality of vertical guide rods 1, an elevation driving mechanism 3 for elevating the table 2, an upper support member 6 provided horizontally across each upper end of the guide rods 1 and having a through hole 4, a spring storing section 7 provided at the location of the through hole 4 on the upper surface of the upper support member 6, a push spring 8 stored in the spring storing section 7, a piston rod 10 inserted in the through hole 4 and urged downwardly by the push spring 8 and having a resin pressurizing piston 9 at the lower end thereof, a flask F placed on the table 2 and having a resin filling hole 11 at the top thereof, a cylinder 13 having a resin passage 12 that communicates with the resin filling hole 11 at the bottom wall thereof and is located below the piston 9 and a pressure breakable member 14 disposed within the cylinder 13 so that it covers the resin passage 12.

7 Claims, 6 Drawing Sheets

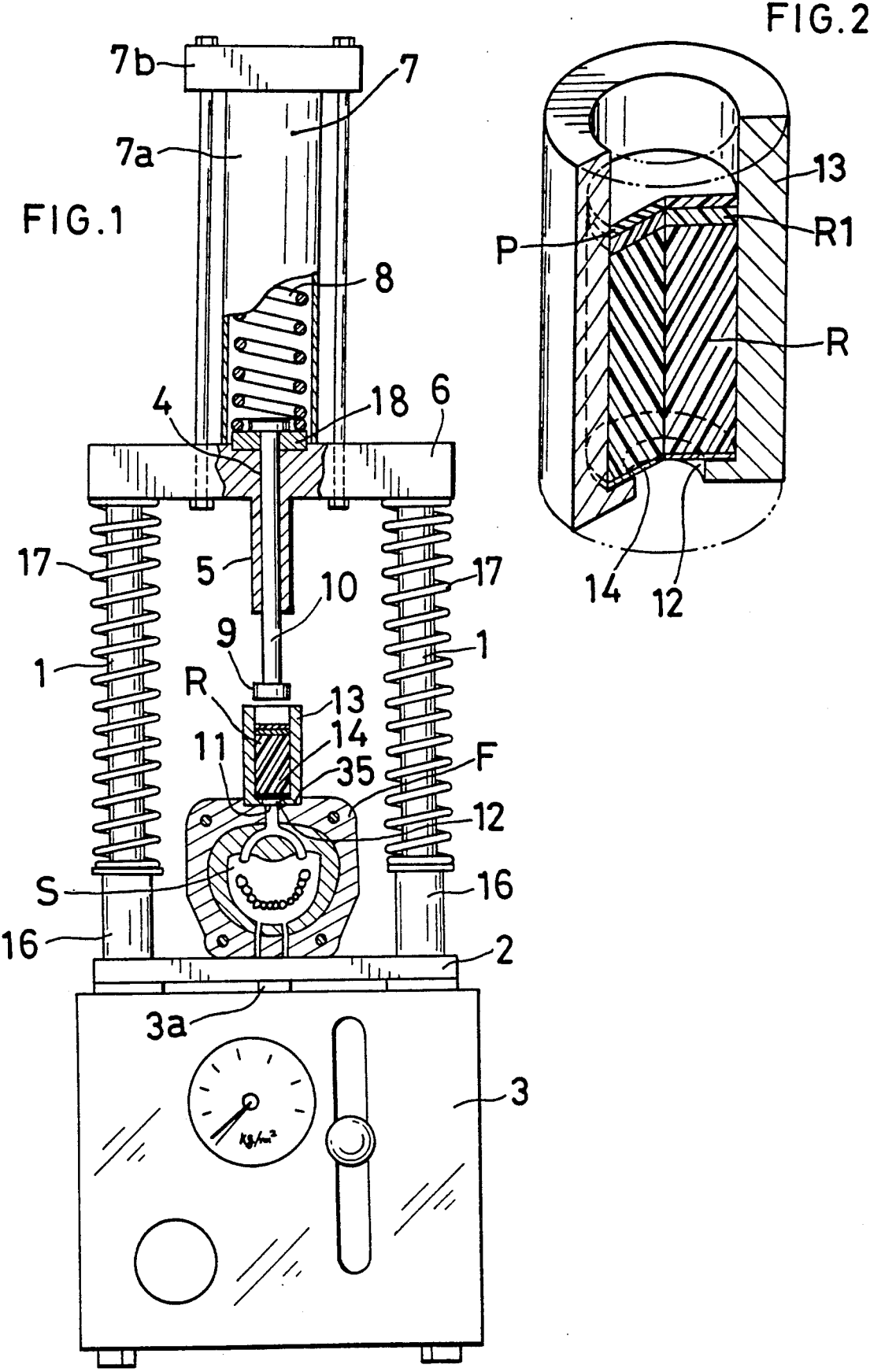

RESIN DENTURE BASE MOLDING APPARATUS

BACKGROUND OF THE INVENTION

1. Field of the Invention

The present invention relates to a denture base molding apparatus and more particularly to a resin denture base molding apparatus for molding denture bases by injecting fused resin in a plaster mold of a denture base formed in a flask.

2. Description of the Related Art

Conventionally, denture bases have been produced by pressurizing and injecting thermosetting resin such as acrylic resin into a plaster mold of a denture base formed in a flask and by polymerizing and solidifying the resin. However, moldings obtained by such method have less accurate dimensions and less shock resistance as well as less abrasion resistance.

In stead of this method, recently a method for obtaining denture bases having excellent shock resistance and abrasion resistance by injecting thermoplastic resin such as polycarbonate resin into a plaster mold of a denture base formed in a flask is being proposed. That is, in a resin denture base molding apparatus for molding denture bases by injecting thermoplastic resin into a plaster mold of denture base in a flask as shown in FIG. 8, resin R is filled into a cylinder 56 from a through hole 53 and is heated and fused by a heater 57. The apparatus comprises a table 51 for placing flask F provided above a hydraulic press unit 50, two support columns 52 provided on the table 51 and lower and upper support members 54 and 58 provided horizontally to the support columns 52. Then, when a piston rod 61 is lowered by a hydraulic cylinder 59, a resin pressurizing piston 60 is inserted to the cylinder 56 through the through hole 53, pressurizing the resin R. The pressurized resin R is injected to denture base plaster mold S in the flask F from a resin injecting hole 55 through a resin filling hole 62, thereby molding the resin denture base.

In the above apparatus, however, the fused resin R filled in the cylinder 56 sometimes leaks out through the resin injecting hole 55, adheres to the resin filling hole 62 and solidifies and clogs the hole before it is pressurized by the piston 60. Therefore, the resin has to be quickly injected after removing resin R adhered to the resin filling hole 62 by a pincette and the like; it causes a difficulty in the operation.

Furthermore, in order to inject the resin R in high speed, the piston rod 61 has to be driven in high speed, so that the hydraulic press unit 50 for supplying hydraulic pressure to the hydraulic cylinder 59 for driving the piston rod 61 becomes very large. Accordingly, this apparatus has such problems that the whole system becomes heavy and costly.

SUMMARY OF THE INVENTION

In view of the aforementioned problems, it is an object of the present invention to provide an improved light weight and low cost resin denture base molding apparatus that enables ultra-high speed injection molding by utilizing resilience of springs for molding resin denture bases by injecting resin into a denture base plaster mold in a flask, and thus to assure moldings having high accuracy to be obtained.

According to the present invention, the improved resin denture base molding apparatus for molding denture bases by injecting fused resin R into a denture base plaster mold S formed in a flask F comprises a table 2 provided in a manner capable of elevating up and down along a plurality of vertical guide rods 1, an elevation driving means 3 for elevating the table 2, an upper support member 6 provided horizontally across each upper end of the guide rods 1 and having a through hole 4, a spring storing section 7 provided at the location of he through hole 4 on the upper surface of the upper support member 6, a push spring 8 stored in the spring storing section 7, a piston rod 10 inserted in the through hole 4 and urged downwardly by the push spring 8 and having a resin pressurizing piston 9 at the lower end thereof, a flask F placed on the table 2 and having a resin filling hole 11 at the top thereof, a cylinder 13 having a resin passage 12 that communicates with the resin filling hole 11 at the bottom wall thereof and is located below the piston 9 and a pressure breakable member 14 disposed within the cylinder 13 so that it covers the resin passage 12.

In the apparatus described above, the pressure breakable member 14 may be a plate or a container made of metal or plastic. Preferably, the pressure breakable member 14 is made of a plastic member having a thickness of 0.1 to 0.6 mm and is set to break with pressurizing force of about 500 to 5000 kg (102 to 1020 kg/cm$^2$).

Although the means having a pressurizing mechanism by means of hydraulic pressure is used as the elevation driving means 3 in the invention, the means is not confined only to that and any means may be used so long as it elevates up and down the table.

According to the improved resin denture base molding apparatus of the present invention, when fused resin is filled in the cylinder 13 in which the pressure breakable member 14 is stored and when the table 2 is elevated by the elevation driving means 3, the piston 9 is inserted into the cylinder 13 pressurizing the resin and in the same time, the push spring 8 is compressed. When the resin is pressurized further and the force pressurizing the resin reaches to a predetermined pressure, the pressure breakable member 14 breaks up. Then in the same time, the piston 9 is pressed down by a repulsive force of the push spring 8 which has been compressed and the resin is injected at a high speed into the plaster mold from the break up point through the resin passage 12 of the cylinder 13 and the resin filling hole 11 of the flask F. Thus resin denture bases having high accuracy may be obtained and the apparatus may be improved to be light-weight and compact, bringing down its cost.

BRIEF DESCRIPTION OF THE DRAWINGS

The invention, both as to its organization and method of operation, together with further objects and advantages thereof may best be understood by reference to the following description taken in connection with the accompanying drawings wherein like parts in each of the several figures are identified by the same reference character wherein:

FIG. 1 is a vertical section view of the whole resin denture base molding apparatus according to a first embodiment of the present invention;

FIG. 2 is a perspective view, with parts broken away and in section, illustrating a state of a cylinder in which resin is filled;

DETAILED DESCRIPTION OF PREFERRED EMBODIMENTS

Figure 3:
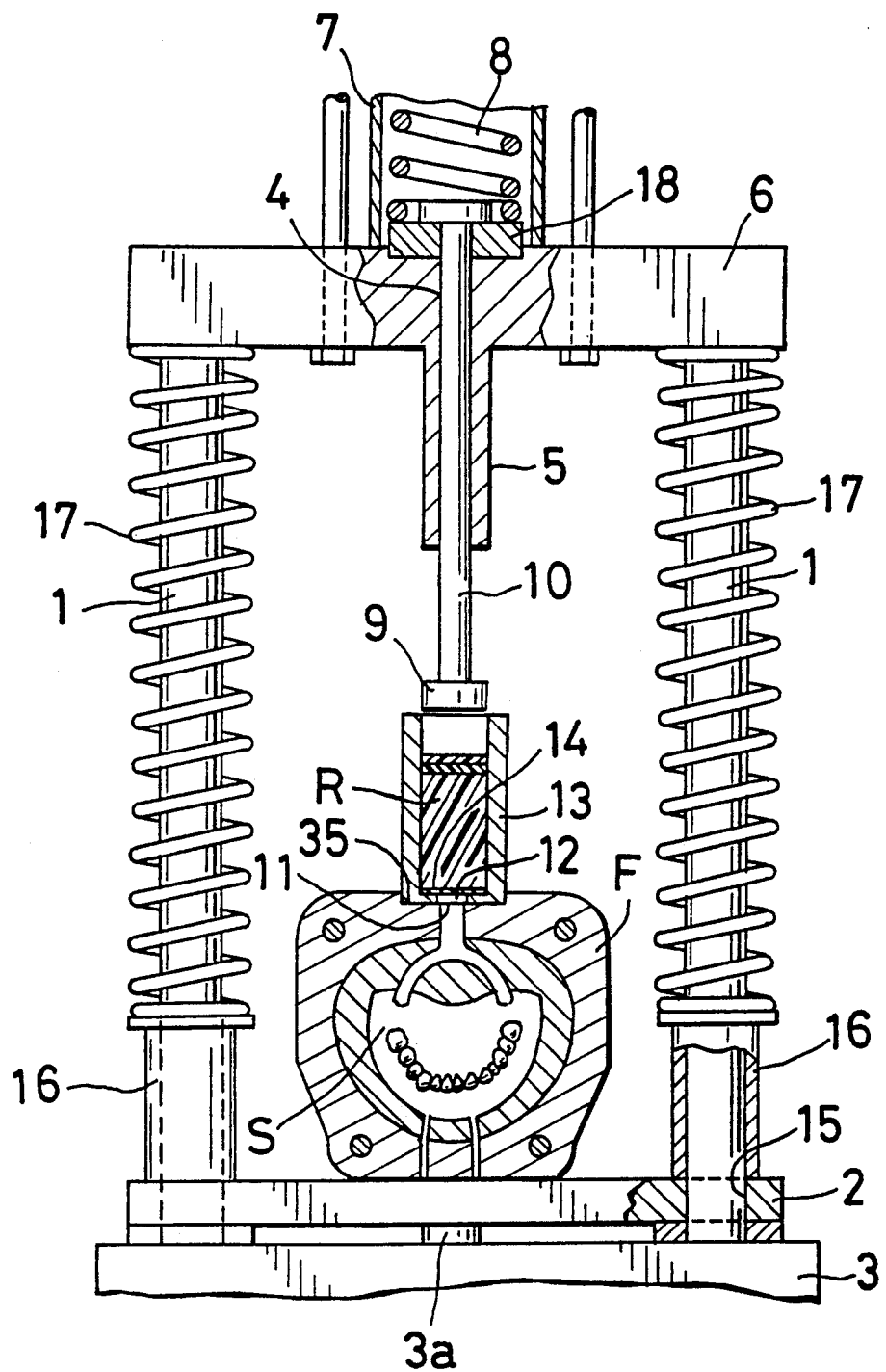
FIG. 3 is an enlarged section view of a main part for showing a state of the apparatus before the resin is pressurized.

Referring now to the drawings, preferred embodiments of the resin denture base molding apparatus of the present invention will be explained in detail.

FIGS. 1 through 5 show a first embodiment of the invention. The resin denture base molding apparatus shown in the figures is an improved type resin denture base molding apparatus for molding denture bases by injecting fused resin R into a denture base plaster mold S formed in a flask F. The improved type apparatus comprises a table 2 provided in a manner capable of elevating up and down along two vertical guide rods 1, a hydraulic press unit 3 for elevating the table 2 by driving up and down a rod 3a by a hydraulic mechanism thereof, an upper support member 6 provided horizontally across each upper end of the guide rods 1 and having a through hole 4 as well as a slide bush 5 protruding downwardly having a passage linked with the through hole 4, a spring storing section 7 provided and fixed at the location of the through hole 4 on the upper surface of the upper support member 6, a push spring 8 stored in the spring storing section 7, a piston rod 10 inserted in the passage of the through hole 4 and the slide bush 5, urged downwardly by the push spring 8 and having a resin pressurizing piston 9 at the lower end thereof, a flask F placed on the table 2 and having a resin filling hole 11 at the top thereof, a cylinder 13 having a resin passage 12 that communicates with the resin filling hole 11 at the bottom wall thereof and is located below the piston 9 and an aluminum plate 14 disposed within the cylinder 13 so that it covers the resin passage 12.

Figure 6:
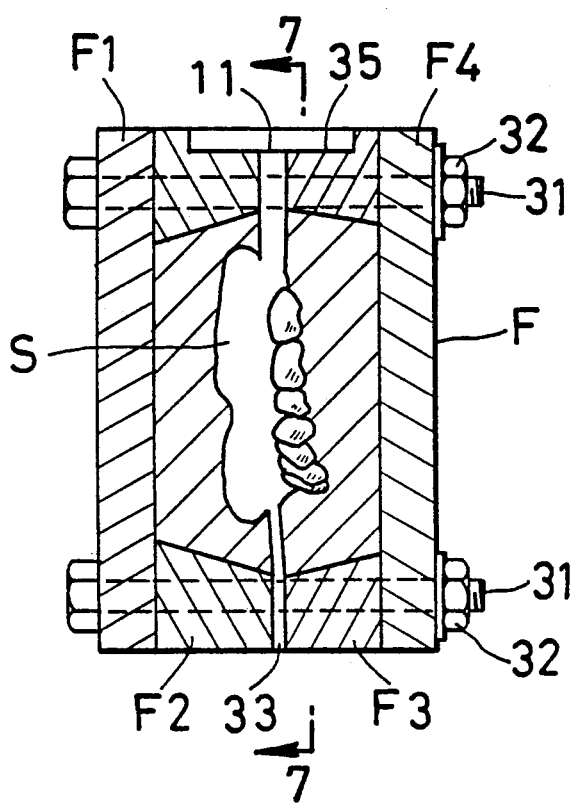
FIG. 6 is a vertical section view of a flask.
Figure 7:
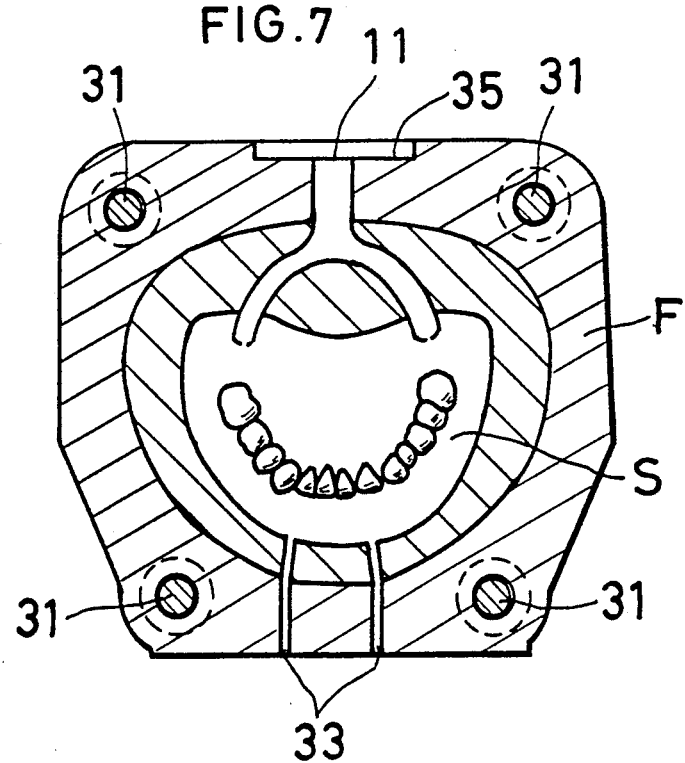
FIG. 7 is a section view taken along line VII—VII in FIG. 6.
Figure 8:
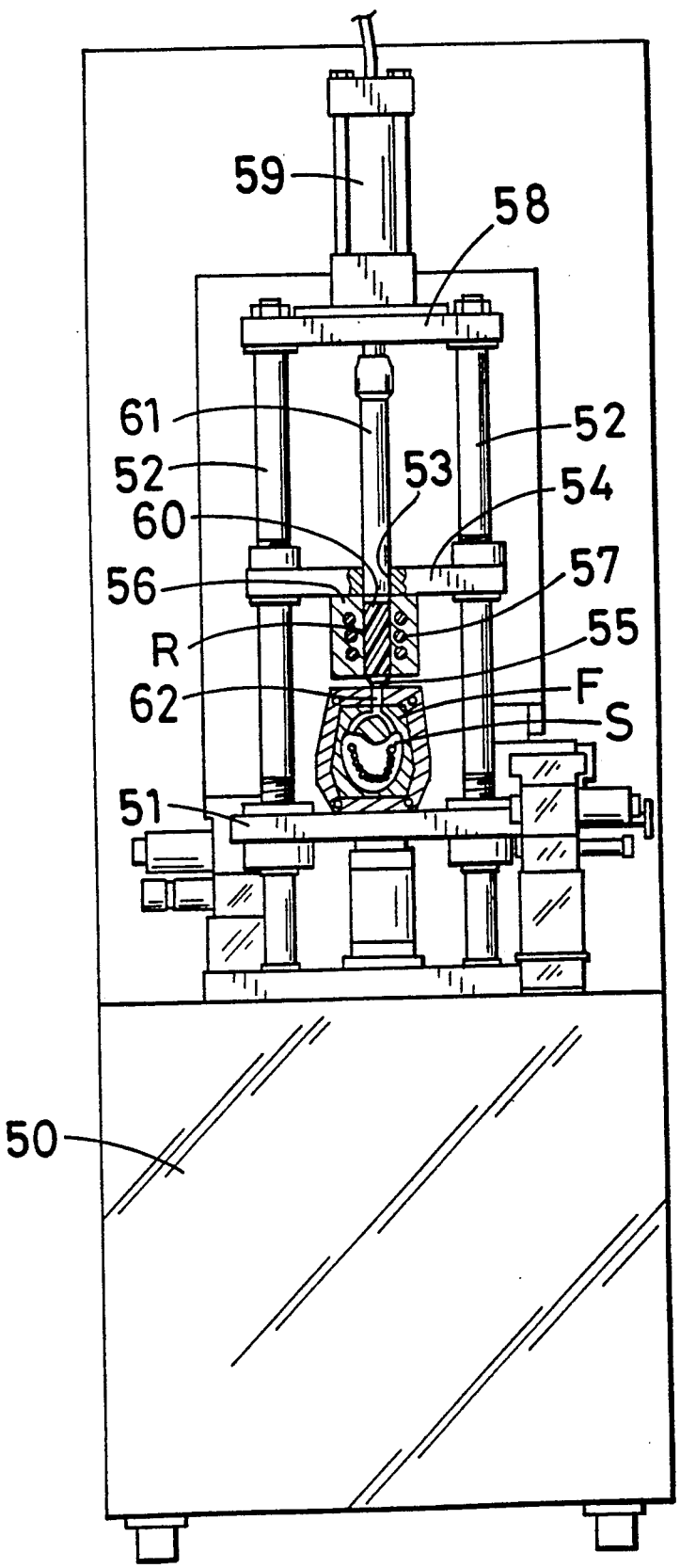
FIG. 8 is a vertical section view illustrating a prior art resin denture base molding apparatus.

Provided on the table 2 are table through holes 15 for inserting the guide rods and table slide bushes 16 protruding upwardly having passages that communicate with the table through holes 15. Table elevation releasing springs 17 which are compressed between the upper support member 6 and the table slide bushes 16 when the table 2 elevates are coiled around the guide rods 1. The spring storing section 7 is structured by a peripheral wall section 7a and a lid 7b for covering the upper opening of the peripheral wall section 7a. Provided at the upper end of the piston rod 10 is a spring presser plate 18. The slide bush 5 is adapted so that the lower end portion thereof abuts on the upper surface of the piston 9 when the piston rod 10 elevates. In this embodiment, the aluminum plate 14 has 0.6 mm of thickness and is set to break with a pressurizing force of about 5000 kg (1020 kg/cm$^2$). The flask F is structured by right and left flask lids F1 and F4 and left and right side flasks F2 and F3 which are connected and secured by a plurality of bolts 31 and nuts 32 as shown in FIGS. 6 and 7. The plaster mold S of denture base in the flask F may be formed by normal methods conventionally used.

Next, a process for injecting thermoplastic resin into the denture base plaster mold S within the flask F using the improved resin denture base molding apparatus of the invention will be explained. By the way, it is preferable to open the flask once to apply photosetting resin on the surface of the plaster mold S and to harden the photosetting resin by irradiating ultraviolet rays and visual light before entering into this process. By doing so, the thermoplastic resin may be prevented from degrading by evaporated moisture in the plaster when the thermoplastic resin is injected into the plaster mold.

At first, the plate 14 is disposed on the bottom wall of the cylinder 13 which is then placed in a concave section in an aluminum block of a resin fusion furnace (not shown). Then, thermoplastic resin R such as polysulfone resin or reinforced polycarbonate resin is charged into the cylinder 13 and is heated and melted while pressurizing using a pressurizing rod. When the resin R completely melts, a small amount (about 5 g) of non-fused resin R1 is charged into the cylinder 13. By doing so, a layer of non-fused resin R1 is formed above a layer of the fused resin R, so that the fused resin R may be prevented from flowing backwardly when it is pressurized. A silicon packing P is provided in the cylinder 13 taken out of the resin fusion furnace as shown in FIG. 2.

Then as shown in FIG. 3, the cylinder 13 in which the fused resin R is stored is placed on a concave portion 35 of the flask F so that the resin filling hole 11 communicates with the resin passage 12. These are set on the table 2. It is desirable to provide concave portions or marks for positioning the flask F on the table beforehand to be able to locate the cylinder 13 below the resin pressurizing piston 9.

Figure 4:
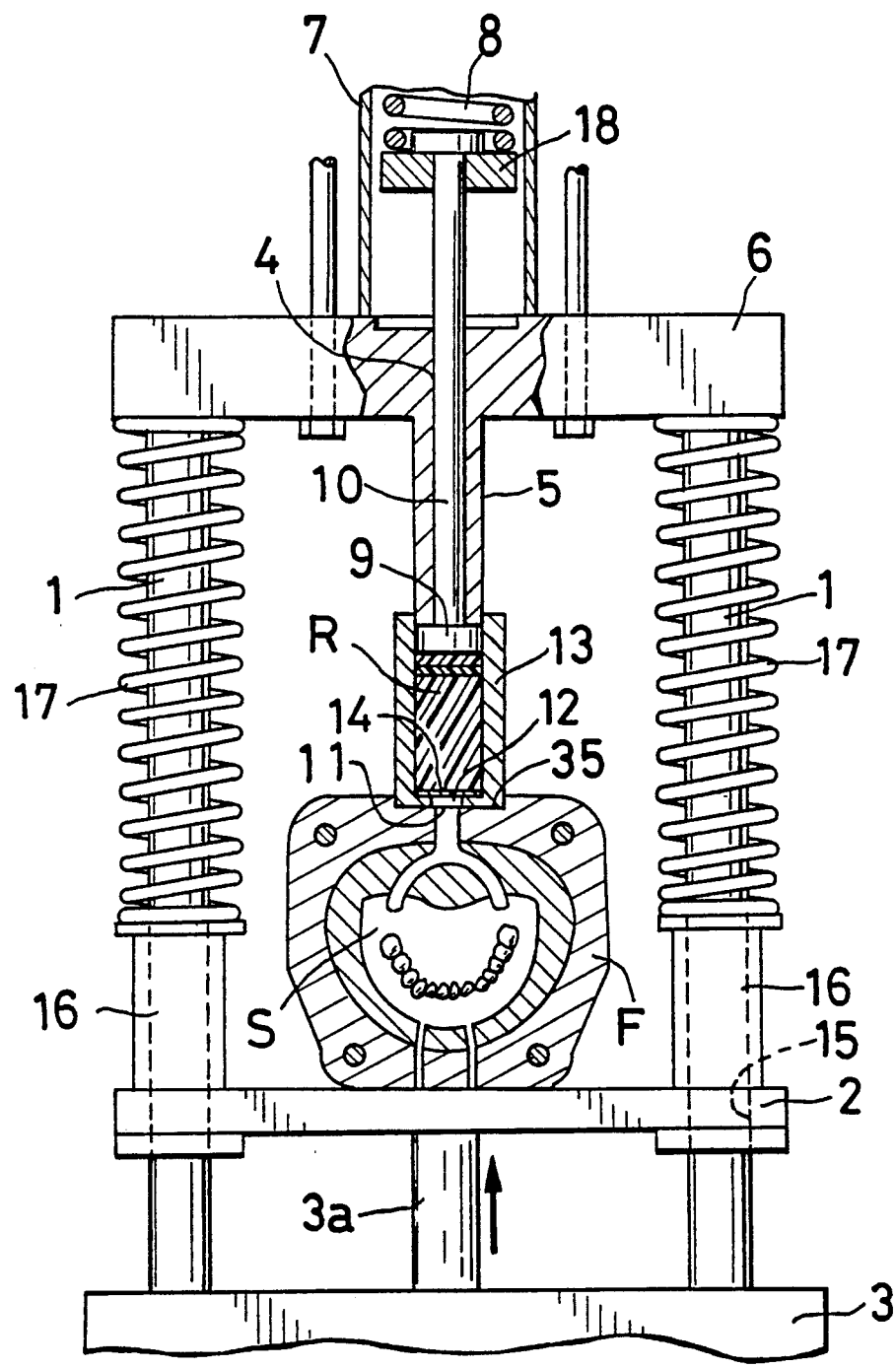
FIG. 4 is an enlarged section view of the main part for showing a state of the apparatus when the resin is pressurized.
Figure 5:
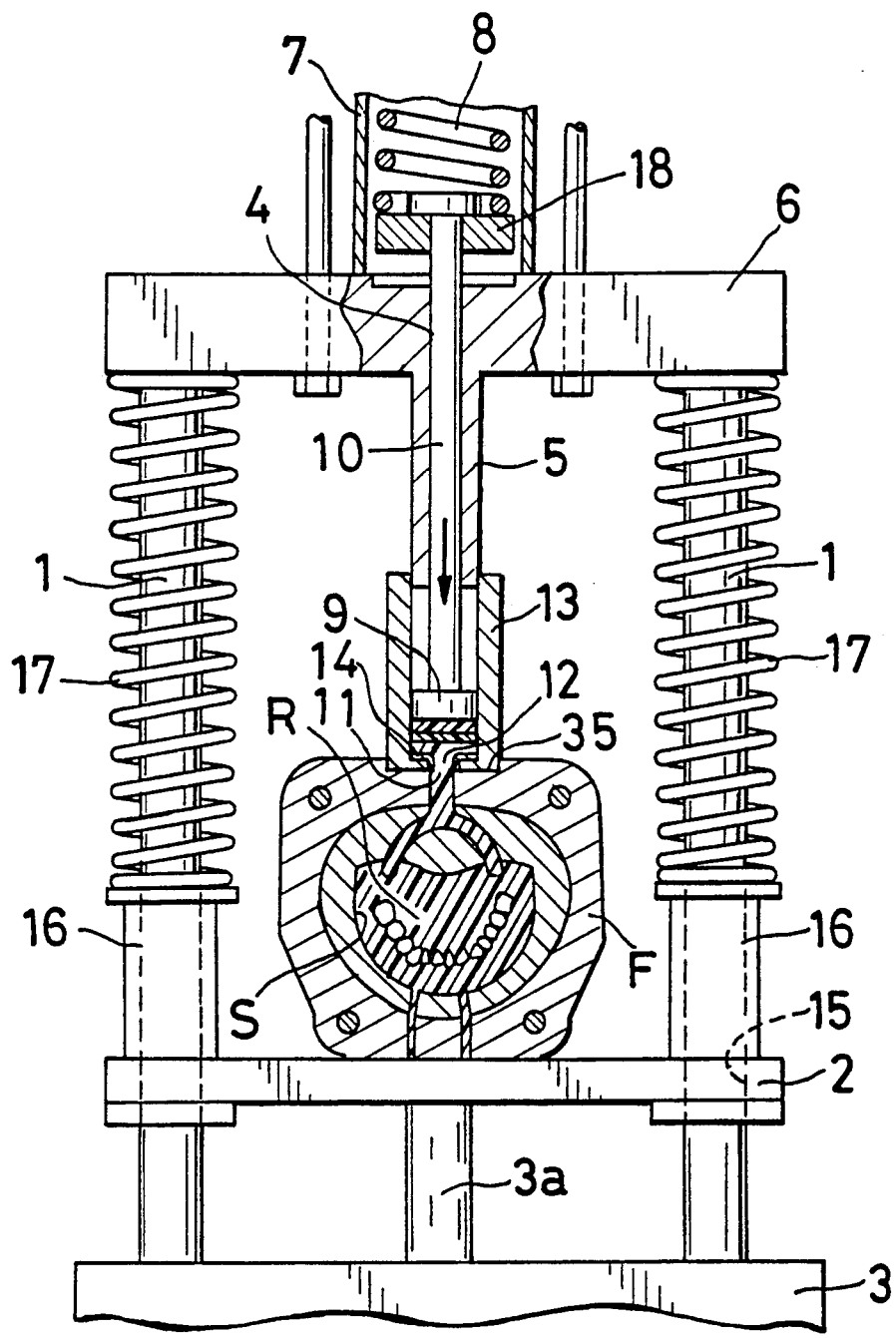
FIG. 5 is an enlarged section view of the main part for showing a state of the apparatus after the resin has been injected.

When the hydraulic press unit 3 is driven, the rod 3a is lifted up by the hydraulic mechanism and thereby the table 2 is elevated. Then the resin pressurizing piston 9 is inserted to the cylinder 13 and the resin R is pressurized by the resin pressurizing piston 9. In the same time, the push spring 8 is compressed by the spring presser plate 18. Next, as shown in FIG. 4, the upper surface of the resin pressurizing piston 9 abuts on the lower end portion of the slide bush 5 and the resin R is further pressurized by the resin pressurizing piston 9. At this time, the lower end portion of the slide bush 5 is inserted within the cylinder 13 together with the resin pressurizing piston 9 and the push spring 8 is still being compressed. When the hydraulic press unit 3 is driven further to pressurize the resin R by the resin pressurizing piston 9 and when the pressurizing force reaches to about 5000 kg (1020 kg/cm$^2$), the plate 14 breaks up and in the same time, the resin pressurizing piston 9 is pressed down in high speed by a repulsive force of the push spring 8 which has been compressed. Then the resin R is injected into the denture base plaster mold S from the break-up point through the resin passage 12 of the cylinder 13 and the resin filling hole 11 of the flask F in high speed. When the resin R is filled in the plaster mold S, the resin pressurizing piston 9 stops dropping, though about 20 kg/cm$^2$ of pressurizing force is maintained by the push spring 8.

The fused resin R injected into the denture base plaster mold S in the flask F naturally hardens when it is left for a while and the temperature thereof drops. After the resin has hardened, the flask F is opened to take out the moldings inside thereof. The moldings obtained by injecting resin R contains a little internal stress, so that it is desirable to release the internal stress by heating up the flask F for about 1 hour in 100° to 130° C. before taking out the moldings as a method for improving the accuracy of the moldings. Resin denture bases having better accuracy and excellent shock resistance and abrasion resistance may be thus obtained.

Figure 9:
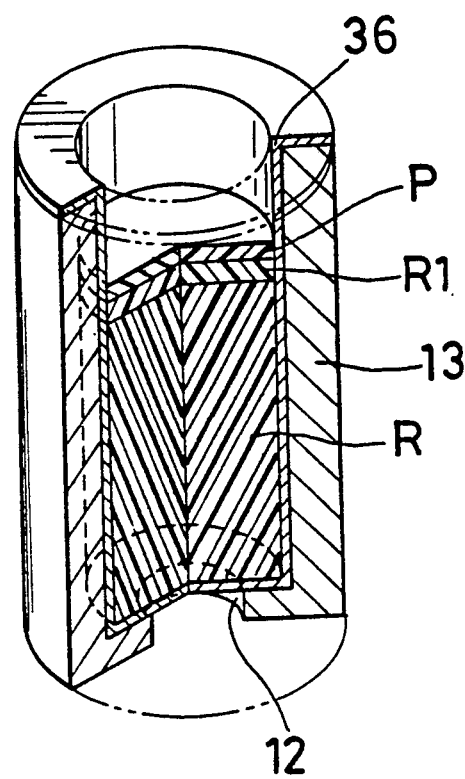
FIG. 9 is a perspective view, with parts broken away in section, illustrating a state of a cylinder, in which resin is filled, of a resin denture base molding apparatus according to a second embodiment of the present invention.

FIG. 9 shows a second embodiment of the apparatus of the present invention. In the apparatus of this embodiment, an aluminum cylindrical container 36 having a bottom is loaded within the cylinder 13. The bottom wall of the container 36 has 0.6 mm of thickness and is designed to break up by about 5000 kg (1020 kg/cm²) of pressurizing force. The other structure is the same as that of the first embodiment. Resin denture base moldings may be obtained in the same way as the case of the first embodiment.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. A resin denture base molding apparatus for molding denture bases by injecting fused resin, comprising:
    a table provided in a manner capable of elevating up and down along a plurality of vertical guide rods;
    an elevation driving means for elevating said table;
    an upper support member provided horizontally across each upper end of said guide rods and having a through hole;
    a spring storing section provided at a location of said through hole on an upper surface of said upper support member;
    a push spring stored in said spring storing section;
    a piston rod inserted in said through hole, urged downwardly by said push spring and having a resin pressurizing piston at the lower end thereof;
    a flask having a denture base mold placed on said table and having a resin filling hole at the top thereof;
    a cylinder having a resin passage that communicates with said resin filling hole at a bottom wall thereof and located below said piston; and
    a pressure breakable member disposed within said cylinder so that the pressure breakable member covers said resin passage; and
    wherein said piston rod has an abutment surface which abuts a fixed member when said piston is pushed against the resiliency of the spring to a completely retracted position, said fixed member being fixed relative to said upper support member.

2. The apparatus according to claim 1, wherein said pressure breakable member is a plate made of metal or plastic.

3. The apparatus according to claim 1, wherein said pressure breakable member is a container made of metal or plastic.

4. The apparatus according to claim 2, wherein said plate is made of aluminum and has a 0.1 to 0.6 mm thickness to be broken up by pressurizing force of about 500 to 5000 kg (102 to 1020 kg/cm²).

5. The apparatus according to claim 3, wherein at least a bottom portion of said container is made of aluminum and has 0.1 to 0.6 mm of thickness to be broken up by pressuring force of about 500 to 5000 kg (102 to 1020 kg/cm²).

6. The apparatus according to claim 1, wherein said abutment surface is an upper surface of said resin pressurizing piston and said fixed member is a slide bushing which extends from a lower surface of said upper support member.

7. The apparatus according to claim 1, wherein said spring is constructed such that at said completely retracted position when said fixed member contacts said abutment surface, said spring exerts an initial outward force which is less than a force required to break said pressure breakable member, and said pressure breakable member is constructed such that further compression force beyond said initial outward force is required to break said pressure breakable member, said further compression force being providable by elevating said table further by said elevation driving means.

* * * * *